United States Patent [19]  
Cheeseman

[11] Patent Number: 5,302,509  
[45] Date of Patent: Apr. 12, 1994

[54] METHOD FOR SEQUENCING POLYNUCLEOTIDES

[75] Inventor: Peter C. Cheeseman, Palo Alto, Calif.

[73] Assignee: Beckman Instruments, Inc., Fullerton, Calif.

[21] Appl. No.: 661,750

[22] Filed: Feb. 27, 1991

Related U.S. Application Data

[63] Continuation of Ser. No. 393,586, Aug. 14, 1989, abandoned.

[51] Int. Cl.$^5$ .............. C12Q 1/68; C12P 19/34; C07H 21/04
[52] U.S. Cl. .................. 435/6; 536/24.33; 536/25.3; 935/77; 935/78
[58] Field of Search .............. 435/6, 91; 536/27, 25.3, 536/24.33; 935/77, 78

[56] References Cited

U.S. PATENT DOCUMENTS 5,001,051 3/1991 Miller et al. .................. 435/6

FOREIGN PATENT DOCUMENTS 8909282 10/1989 PCT Int'l Appl. .................. 435/6

OTHER PUBLICATIONS

"A Photoinduced Cleavage of DNA Useful for Determining T Residues", A. Simoncsits et al., Nucleic Acids Research, vol. 10/No. 24 (1982) pp. 7959–7965.
"Molecular Biology", Second Edition, D. Freifelder, pp. 85–86.
"Primer-Directed Enzymatic Amplification of DNA with a Thermostable DNA Polymerase", R. Saiki et al, Science, vol. 239, pp. 487–491.
"Light-Directed, Spatially Addressable Parallel Chemical Synthesis", S. Fodor et al, Science, vol. 251, pp. 767–773.
"Photoremovable Protecting Groups in Organic Synthesis", V. N. Rajasekharan, Synthesis, 1980, pp. 1–26.
"Organic Chemistry of Nucleic Acids", N. Kochetkov et al, Part B, Plenum Press (1972) Chapter 9, pp. 449–476.
"Automated DNA Sequencing: Ultrasensitive Detection of Fluorescent Bands During Electrophoresis", W. Ansorge et al., Nucleic Acids Research, vol. 15/No. 11 (1987) pp. 4593"4602.
"Solid Phase DNA Sequencing Using the Biotin–Avidin System", S. Stahl et al, Nucleic Acids Research, vol. 16/No. 7 (1988) pp. 3025–3038.
"Automated DNA Sequence Analysis", C. Connell et al., BioFeature, vol. 5, No. 4 (1987) pp. 342–348.
"Molecular Biology and Biotechnology", J. Walker et al., Second Edition, p. 352.
"A System for Rapid DNA Sequencing with Fluorescent Chain-Terminating Dideoxynucleotides", J. Prober et al., Science, vol. 238, Oct. 16, 1987, pp. 336–341.
"A New Procedure for Determining Thymine Residues in DNA Sequencing. Photoinduced Cleavage of DNA Fragments in the Presence of Spermine", I. Saito et al., Nucleic Acids Research, vol. 12/No. 6 (1984) pp. 2879–2885.

(List continued on next page.)

Primary Examiner—Mindy B. Fleisher
Attorney, Agent, or Firm—William H. May; P. R. Harder; Janis C. Henry

[57] ABSTRACT

A method is provided for determining the sequence of nucleotides on a single strand DNA molecule. The single strand DNA molecule is attached to a leader oligonucleotide and its complementary strand to a solid state support. Fluorescently-labeled 3'-blocked nucleotide triphosphates, with each of the bases A, G, C, T having a different fluorescent label, are mixed with the bound DNA molecule in the presence of DNA polymerase. The DNA polymerase causes selective addition of only the complementary labeled NTP, thus identifying the next unpaired base in the unknown DNA strand. The 3'-blocking group is then removed, setting the system up for the next NTP addition and so on. The sequence is repeated until no more fluorescently-labeled NTPs can be detected as being added by the polymerase.

10 Claims, 2 Drawing Sheets

OTHER PUBLICATIONS

"Optimized Conditions for Solid-Phase Sequencing: Simultaneous Chemical Cleavage of a Series of Long DNA Fragments Immobilized on CCS Anion-Exchange Paper", A. Rosenthal et al, Gene 42 (1986) pp. 1-9.

"New Sequences to Take on the Genome", L. Smith, Research News (1987) pp. 271-272.

"Selective Inhibition of DNA Chain Elongation Catalyzed by DNA Polymerase", A. Krayevsky et al., Nucleosides & Nucleotides, 7 (5&6) pp. 613-617 (1988).

"Fluorescence Detection in Automated DNA Sequence Analysis", L. Smith et al., Nature, vol. 321, Jun. 1986, pp. 674-679.

"Direct Solid Phase Sequencing of Genomic and Plasmid DNA Using Magnetic Beads as Solid Support", T. Hultman et al., Nucleic Acids Research, vol. 17/No. 13 (1989) pp. 4937-4946.

"CIV. Total Synthesis of the Structural Gene for an Alanine Transfer Ribonucleic Acid from Yeast, Chemical Synthesis of an Icosadeoxynucleotide Corresponding to the Nucleotide Sequence 21 to 40", H. Weber et al, J. Mol. Biol. (1972) 72, pp. 219-249.

METHOD FOR SEQUENCING POLYNUCLEOTIDES

This application is a continuation of U.S. application Ser. No. 07/393,586 filed Aug. 14, 1989 now abandoned.

The present invention is directed to a method for sequencing DNA molecules.

BACKGROUND OF THE INVENTION

The present invention provides a method for determining the nucleotide sequence of DNA molecules (referred to herein as the nucleotide base sequence or simply the base sequence). Several methods are known for sequencing DNA molecules such as methods of F. Sanger, S. Nicklen, A. R. Coulson, *Proc. Natl. Acad. Sci. U.S.A.*, 74, 5463 (1977), and A. M. Maxam and W. Gilbert, *Proc. Natl. Acad. Sci. U.S.A.*, 74, 560 (1977). These known methods use various means for producing labeled fragments of DNA, each of which terminates with a known base (A, G, C or T). These fragments are then separated by length, typically by an electrophoretic gel, utilizing a different gel strip for each type of terminal base. The DNA sequence is then read from the gel strips. As a variation, instead of using the same label for each fragment (such as a fluorescent dye or radioactive label) J. M. Prober, et al., Science, 238, 336–341, Oct. 1987, and C. Connell et al., BioTechniques, Vol. 5, No. 4, 342–348 (1987), use a different dye to label each of the different base termination fragments so there is a different dye associated with A, G, C and T termination. This modification allows a single gel to be used, however, it also introduces new problems due to the effect of the different dyes on fragment mobility.

A limitation of the prior methods is that they are apparently limited by the rate at which the fragments may be separated and are also limited by the number of bases that can be sequenced in a given run by the resolution obtainable on the gel. The separation rate is inherently limited, for example, by thermal distortion of the gel caused by electrical heating, and thus the identification can only be obtained as often on average as about a few bases per minute. Also the resolution on the gel is a maximum of about 1,000 bases, with improvement in this resolution not being likely because of band compression effects, and because there are interactions between the DNA strands which dominate over the length effect of very long strands, thus confusing the signal for long fragments.

The present invention provides an improvement over these prior art methods.

It is thus an object of the present invention to provide a method of DNA identification in which the rate limiting step is essentially the rate of a polymerase reaction, which is usually on the order of at least 60 bases per second, or limited by the rate in which the reagents can be delivered to the reaction site, whichever is slower.

It is another object of the present invention to provide a method of DNA sequencing in which the accuracy does not depend upon the length of the DNA molecule to be sequenced but, rather on the signal-to-noise ratio of the detection means, which is very low using optical detection methods. Such high sensitivity detection means provide the advantage that only very small quantities of DNA are necessary, typically, less than a million molecules.

It is yet another object of the present invention to provide a DNA sequencing which is unambiguous even in short sequences of identical bases, which are difficult to distinguish by prior art methods.

Another object of the present invention is to provide a novel method for DNA sequencing in which the reagents for detection comprises a single mixture of bases, and does not require four separate preparations (one for each base) as required by methods of the prior art.

These and other objects of the present invention will be apparent from the following description, the appended claims and from practice of the invention.

SUMMARY OF THE INVENTION

The present invention provides a method for determining the nucleotide sequence of a single strand DNA molecule comprising the steps of:

(a) providing a set of identical single strand DNA molecules (ssDNA) comprising at the 3' end a leader sequence, the leader sequence comprising a region recognizable by a DNA polymerase for initiation of replication;

(b) providing an oligonucleotide complementary to at least a portion of the leader sequence, and capable of forming a stable double stranded DNA hybrid therewith;

(c) covalently attaching the 3' end of the leader sequence, the 5' end of the ssDNA or an end of the oligonucleotide to a solid support;

(d) forming a stable double strand DNA hybrid bound to the solid support, the hybrid comprising the oligonucleotide and the single stranded DNA molecule with the leader sequence and the bound hybrid acting as a primer for DNA polymerase replication;

(e) exposing the hybrid bound to the solid support to a DNA polymerase in the presence of fluorescently-labeled 3'-blocked derivatives of the four nucleotide 5'-triphosphates of 2'-deoxyadenosine, 2'-deoxyguanosine, 2'-deoxycytidine and 2'-deoxythymidine, where each of the four nucleotide 5'-triphosphate (NTPs) derivatives is labeled with a fluorescent label distinguishable by fluorescent detection means from the other three labels on the other three nucleotide 5'-triphosphate derivatives, under conditions whereby the polymerase will add the appropriate complementary nucleotide 5'-triphosphate derivative to the oligonucleotide;

(f) separating any unused NTP derivatives from the solid supported DNA hybrid and the support;

(g) identifying the labeled NTP derivative added to the double stranded DNA by optical detection means; thereby identifying its complementary deoxynucleotide present in the single stranded DNA molecule;

(h) removing the fluorescent label and 3' blocking group from the labeled NTP derivative of step (g) to expose the normal OH group in the 3'-position;

(i) separating the freed blocking group and label (which may be associated with the blocking group) from the solid supported double stranded DNA hybrid;

(j) repeating steps (e) through (i) through a plurality of cycles until labeled NTPs can no longer be added to the oligonucleotide; whereby the result of each cycle identifies the next deoxynucleotide in sequence in the single stranded DNA molecule.

BRIEF DESCRIPTION OF THE DRAWINGS

In the accompanying FIG. 1 there is schematically shown a double stranded DNA hybrid bound to a solid support utilized in accordance with the present invention.

In the accompanying FIG. 2 there is illustrated a photolytic removal of a 3'-blocking group from a 3'-blocked nucleotide in accordance with the present invention.

DESCRIPTION OF THE PREFERRED EMBODIMENTS

The purpose of the present invention is to determine the sequence of a set of identical single stranded DNA molecules, therefore it will be assumed that such strands are initially provided. These strands, hereinafter called ssDNA, are adapted to be used in accordance with the present invention. Various ways to adapt the ssDNA for attachment with a complementary oligonucleotide to a solid support will be apparent to those of ordinary skill in the art. Several methods are described herein as preferred embodiments. One method is to modify the ssDNA with a known leader. The purpose of the modification is to attach to the 3' end of the ssDNA a known leader sequence which (when hybridized for form a duplex) is recognizable by the polymerase to be utilized for the initiation of replication unless the provided ssDNA already has a known leader sequence. The 3'-end of the leader may also provide a handle which may be attached to a solid support. The ssDNA may be modified at least in any of the following ways.

One such method is to first amplify the quantity of the ssDNA by polymerase chain reaction techniques (PCR, reference, R. Saiki et al., Science, Vol. 239, 487–491, January 1988). Prior to amplification, if necessary, a known single stranded sequence comprising the single stranded sequence of a sticky end may be added as a short, temporary leader to the ssDNA. Methods of joining the 5' end of one oligonucleotide to the 3' end of another DNA molecule are known in the art and can be routinely performed.

Figure 1:
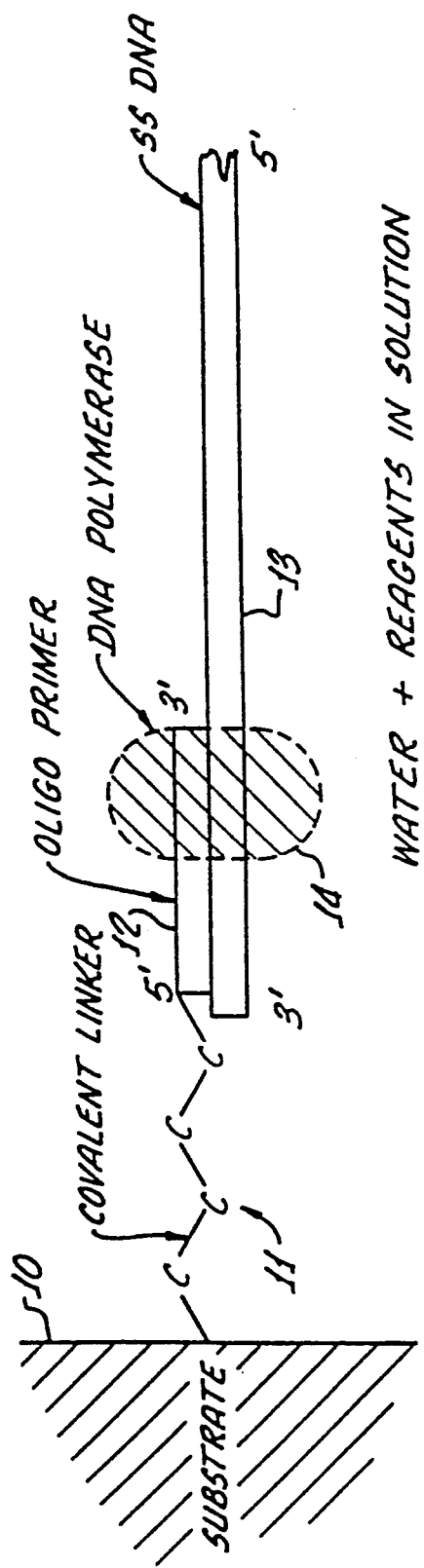

Amplification by PCR creates many such DNA molecules with a short leader. An oligo complementary to the short leader may then be added so that there is a short section of double stranded DNA at the leader, as shown in FIG. 1.

An alternative approach is to attach a double stranded oligo with a sticky end to the solid support. This oligo will have the complementary sequence of the same restriction site used to create the ssDNA. Then the two sticky ends will be ligated to form a double stranded DNA molecule attached to a solid support as shown in the FIG. 1.

Alternatively, a single strand leader may be ligated to the end of the unknown ssDNA strand. The oligo containing a sequence complementary to the leader (or portion thereof) may be bound through its 5' end to the substrate. Then the ssDNA and the associated leader will be bound to the solid support by hybridization to the bound oligonucleotide to result in the identical situation shown in FIG. 1.

Alternatively instead of sticky ends as described above, blunt end ligation may be utilized.

Initially, the double stranded portion of the bound molecule in FIG. 1 will be a primer for a suitable DNA polymerase, preferably Taq polymerase, which is operable at high temperature.

Another starting material required for the present invention is a mixture of four fluorescently-labeled (or other optically labeled such as optical absorption dyes, or chelated ions) 3'-blocked, NTPs (nucleotide triphosphates). The preferred embodiment has the fluorescent label as part of the 3'-blocking group. Each of the NTPs will be labeled by a different label (i.e., each of the A, G, C and T NTPs will have different labels on them) so as to be distinguishable by fluorescent spectroscopy or by other optical means. Such labels are known in the art and are disclosed for example in Prober, et al., *Science*, vol. 238, pp. 336–341 (1987) and Connell et al., *BioTechniques*, Vol. 5, No. 4, 342–384 (1987); Ansorge, et al., *Nucleic Acids Research*, vol. 15 (11) 4593–4602 (1987) and by Smith, et al., *Nature*:321, 674 (Jun. 12, 1986). Each of the NTPs has a 3'-blocking group, so as to prevent the polymerase from continuing to replicate once one base has been added. This is preferably accomplished by having the dye attached through a covalently linking group to the 3'-position so that the dye moiety and the 3'-blocking group are contained in the same substituent. Examples are shown below.

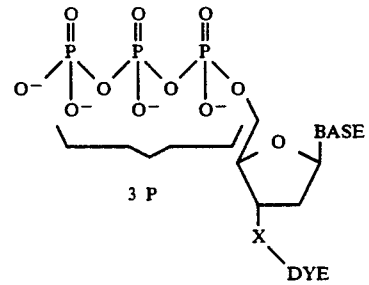

wherein:
X is —O—A— and
A is a functional group which is removable to expose the 3'-hydroxyl group.
For example, A may be

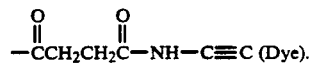

This may be prepared by treating any of the reactive dyes, such as reactive fluorescent dyes functionalized with halo groups, with N-trifluoroacetyl propargylamine under conditions described by Prober et al., *Science*, 238: 336–341, Oct. 1987, then deacylating. This amino-dye may then be coupled to a 3'-O-succinyl protected nucleotide to produce a 3'-O-protected nucleotide wherein the protecting group is

which is removable under conditions similar to that of the O-succinyl protecting group commonly used in solid phase nucleotide synthesis. Alternatively, an acid anhydride, to which the dye is attached, may be directly condensed with the 3'—OH group. Thus to initiate the sequencing, the bound double strand DNA molecule shown in FIG. 1 is exposed to the DNA polymerase and a mixture of the four fluorescently-labeled 3'-blocked NTPs. The polymerase will then add one of the four NTPs to the growing oligonucleotide chain, whichever NTP is complementary to the next unpaired base in the ssDNA. This step is rapid since the average reaction rate of adding a base to an oligonucleotide with a polymerase is in the range of at least 60 bases per second. Since only one base is being added this can be accomplished in less than a second.

The next step is to separate the unused NTP's from the vicinity of the support bound DNA by washing. Since it is possible for the free NTPs to bind to the ssDNA, the wash should take place at a temperature so that the free NTPs do not bind to the ssDNA, but not high enough to dehybridize the double stranded DNA. In order not to deactivate the polymerase at such a temperature, it is preferred that a high temperature polymerase be utilized such as the aforementioned taq polymerase. Since the double stranded DNA is in the environment of a solid support, it is also required that the solid support surface not attract the NTPs, so Teflon or similarly non-adhering lining for the solid support should be utilized. The wash which is used to wash the free NTPs from the support bound double stranded DNA may be any convenient wash such as buffered saline, or polymerase buffer without the NTPs.

Washing is also a rapid step since it is contemplated that one would only be using small quantities of DNA concentrated in a small area. The washing should only take around a few seconds or less.

Since only one of the four types of NTPs will be added to the oligonucleotide, it may be read by its fluorescent label using a suitable fluorescent detection means. According to the preferred embodiment of the present invention this may be done by making the solid support for the bound DNA the end of an optical fiber. By transmitting the radiation of appropriate exciting wavelength through the fiber, the labelled DNA at the end of the fiber will fluoresce and emit the light of appropriate fluorescent frequency. The emitted fluorescent light will be partially transmitted back into the optical fiber in the reverse direction to the exciting light.

This back propagating light can be separated spectrally by such means as an etched diffraction grating on the fiber. The returned light spectrum identifies the particularly bound NTP. It will be within the skill of those of ordinary skill in the art to adjust the concentration of the bound DNAs such that there will be a sufficient number of fluorescent molecules present for optical detection by this means.

It is preferred that the fluorescent dye marker and the 3'-blocking group be present in the same substituent, for example as shown below.

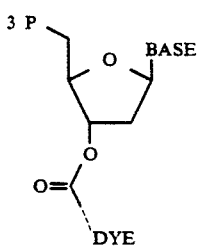

The identification of the bound NTP identifies its complementary base as the first unpaired base in the unknown sequence of the ssDNA.

The next step is to remove the 3'-block and associated fluorescent label from the bound NTP to prepare for the addition of the next NTP onto the oligonucleotide. This removal may be accomplished by chemical means or photochemical means. The chemical means of removing the 3'-blocker will of course depend upon the nature of the 3'blocking groups, many of which are known in the art as shown for example in Chapter 1, *Organic Chemistry of Nucleic Acids*, Part B, Eds. N. K. Kochetkov and E. I. Budovskii, Plenum Press, 1972 and H. Weber and H. G. Khorana, *J. Mol. Biol.*, 72, 219-249 (1972). Methods of their removal are therefore also known.

Figure 2:
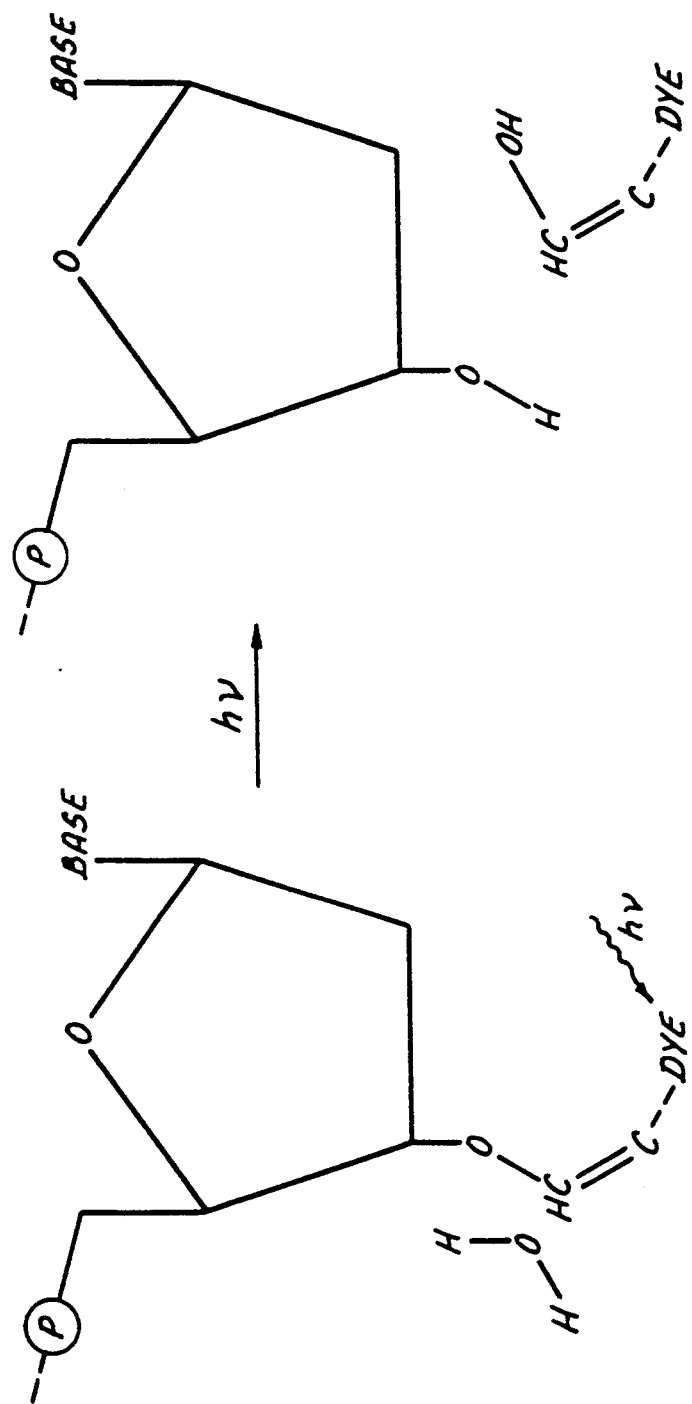

Preferably the fluorescent label and 3'-blocker may be removed quickly by photolysis, as shown in FIG. 2. In the photolysis reaction, instead of the absorbed light energy being re-emitted as fluorescent light, it is occasionally conveyed to the 3' position by means of an alternating single-double bonds hydrocarbon chain. The excitation energy can then catalyse (or enable) the hydrolysis of the acyl group, as shown, Even after cleavage of the dye label, it is still present in the vicinity for optical identification. The dyes are chosen with fluorescent emission spectra that are as well separated as possible but which can be activated preferably by the same exciting source. Thus the only significant limitation to detection is the signal-to-noise ratio due to the Rama scattering of the other materials present, particularly water. By using activation wavelengths which minimize Raman scattering from water the signal-to-noise ratio will be improved.

The solid-supported ssDNA will be scanned for the optical labels preferably using a optical fiber. The end of the fiber may simply be brought close to the surface of the support for detection, or the end of the fiber may itself be the solid support. An alternative means is to attach the DNA to the sides of the core of an optical fiber (by removing the cladding from a selected area). If attached to the sides of an optical fiber, the DNA is illuminated by evanescent lighting surrounding the fiber, and only light emission in this region can couple back into the fiber.

Concentration of the dye in a small area will also improve detection by increasing the ratio of fluorescent material to background Rama scattering solution. The optical fiber improves the signal-to-noise ratio compared to methods of the prior art since the prior art illuminates comparatively large volumes. Also the use of an optical fiber to bring the light to the reaction area and to carry the fluorescent output away is simple and can be used to separate the return light into spectral bands which can be then detected by small solid state-like detection means such as PIN photodiodes. Spectral separation may be accomplished for example., by periodic diffraction grading etched into the fiber or by using a cladding with a higher dispersion than the core so that different wavelengths will or will not satisfy the critical angle condition. Wavelengths that do not satisfy the critical angle condition will escape into the cladding where they can be detected. Utilizing solid state components, the whole sequencing cell, including the optical detection means may be provided in a planar integrated optical system, which can thus be produced by photolithographic means, as disclosed, for example in *Planar Optical Waveguides and Fibres*, H. G. Unger, Clarendon Press, Oxford (1977). Planar optics also allows many sequencing cells to be produced on the same substrate and illuminated by the same light source. Signal-to-noise ratios can be further improved by using time resolved fluorescence (TRF), with relatively long-lived fluorescent species (e.g., chelated rare earth ions). By this method the detection occurs after the Raman scattering has subsided, but the fluorescent species are still in the emission mode, as disclosed in I. Hemmila, et al., Anal. Biochem. 137, 335-343 (1984), for example.

Once the fluorescent label and 3'-blocker (which are preferably one and the same) are removed from the labeled bound NTP, they are separated from the bound DNA by washing, using, for example, washing reagents described above.

Then the sequence beginning with exposure to the polymerase and the four labeled 3'-block NTPs is repeated, with each cycle adding another base to the growing oligonucleotide, thereby identifying the next base in the unknown ssDNA sequence and so on. The identification is completed when a cycle fails to show that a label is present after the polymerase reaction and washing step.

According to a preferred embodiment of the present invention, the double stranded DNA is attached onto the end of an optical fiber, and the end of the fiber may be dipped into each of the reagents in turn. By moving or vibrating the fiber, there will be rapid mixing of the boundary layer in the bulk reagent.

Simple flow systems may be used to bring the reagents to the active part of the fiber, such as capillary electrophoresis or hydrostatic pressure, connected to the appropriate reagents.

It is expected that all of the bound DNA molecules will start at the same position on the ssDNA and add the same type of NTP during each cycle of the process. Due to imperfect mixing or the dynamics of a densely populated surface the rate of adding NTPs to each of the solid state-bound DNAs may not be identical. Therefore some of the strands may fall behind in the sequence of adding an NTP. For example, if a 3'-blocker remains after the block removal step for a particular DNA unit, that blocker may not be removed until the next cycle and therefore that particular strand will fall behind by addition of one NTP unit. The symptoms of the loss of synchronization of adding an NTP will be the appearance in the fluorescent spectra of dyes other than the majority dye being detected for the NTP which was added. As long as the interfering fluorescent spectra do not interfere substantially with detection of the majority dye being added in the cycle of interest, this need not be a concern. For sufficiently long ssDNA, the accumulation of errors may require re-synchronization, forcing the lagging DNA to catch up with the current DNA. This resynchronization can be achieved by changing the reaction mixture of the NTPs, and having two identical reaction cells, one running a few bases ahead of the other. For example if the sequence in the leading cell is ACGTTC, and the trailing cell is one base behind (i.e., ACGTT); then instead of adding the usual four blocked NTPs to the trailing cell, blocked C, A, G may be added with unblocked T. Those DNA units that are behind in the trailing cell (e.g., ACGT or ACG) add the unblocked T (or TT), followed by a blocked C, while the majority will just add the blocked C. The leading cell is necessary so that the next base for the majority of the trailing cell is known, and so an unblocked NTP can be added without interfering with the process. The roles of leading and trailing cells can be switched so that one can act as the predictor for the other, and vice versa.

Referring to FIG. 1 there is shown a solid substrate 10 covalently linked through a linker 11. In the FIGURE the linker 11 is attached to the 5' end of the oligonucleotide 12, however it may also be attached to the 3' end of the ssDNA 13. The shaded area 14 is the DNA polymerase, which is primed by the oligo bound to the ssDNA.

Having described the preferred embodiments of the present invention various modifications will be evident to those of ordinary skill in the art from the above description as well as from practice of the invention. These modifications are intended to be within the scope of the invention and the invention is not intended to be limited in any way except by the scope of the following claims.

What is claimed is:

1. A method for determining the nucleotide sequence of identical single strand DNA molecules comprising the steps of:

(a) providing said single strand DNA molecules at their 3' end with a known leader sequence, said leader sequence forming a double stranded DNA hybrid with an oligonucleotide having a sequence complementary to said leader sequence;

(b) providing to said leader sequence said oligonucleotide having a sequence complementary;

(c) covalently attaching either the 3' end of said leader or the 5' end of said oligonucleotide to a solid support;

(d) forming a stable double stranded DNA hybrid, said hybrid comprising said oligonucleotide and said leader;

(e) exposing said hybrid to a DNA polymerase in the presence of optically-labeled derivatives of four nucleotide 5'-triphosphates of 2'-deoxyadenosine, 2'-deoxyguanosine, 2'-deoxycytidine and 2'-deoxythymidine, where said optically-labeled derivatives comprise a blocking group at the 3' portion thereof, said blocking group comprising an optical label capable of being removed to expose the 3' portion thereof, where each of said four derivatives is labeled with an optical label distinguishable by an optical detection means capable of detecting said optical label from the other three labels on the other three of said derivatives under conditions whereby said polymerase will add the complementary optically-labeled 3'-blocked nucleotide 5'-triphosphate to said oligonucleotide;

(f) washing any unused derivatives from said double stranded DNA hybrid;

(g) detecting the labeled derivative incorporated onto the double stranded DNA hybrid by said optical detection means thereby identifying the complement of said optically-labeled 3'-blocked nucleotide 5'-triphosphate added to said oligonucleotide present in said single stranded DNA molecules;

(h) removing, by chemical means or photochemical means, the optically-labeled 3'-blocking group from the derivative incorporated in step (g) to expose the OH group in the 3' position; of the nucleotide 5'-triphosphate derivative incorporated into the double stranded DNA hybrid (i) separating the removed optically-labeled blocking group from said double stranded DNA hybrid;

(j) repeating steps (e) through (i) through a plurality of cycles until labeled nucleotide 5'-triphosphate derivatives can no longer be added to said oligonucleotide, whereby the result of each cycle identifies the next deoxynucleotide in sequence in said single stranded DNA molecules.

2. A method according to claim 1 wherein said polymerase comprises Taq polymerase.

3. A method according to claim 1 wherein said optical labels comprise fluorescent derivatives which fluoresce upon excitation thereof by irradiation with an appropriate radiation wavelength.

4. A method according to claim 3 wherein said optical labels are a part of said 3'-blocking group.

5. A method according to claim 4 wherein said 3'-blocking group is removed from said nucleotide triphosphates by photochemical activation.

6. A method according to claim 1 wherein the 3' end of said leader is attached to said single stranded DNA molecule by polymerase chain reaction amplification.

7. A method according to claim 1 wherein the 3' end of said leader is attached to said single stranded DNA molecule by blunt end ligation.

8. A method according to claim 1 wherein the 3' end of said leader is attached to said single stranded DNA molecule by sticky end ligation.

9. A method according to claim 1 wherein said solid support comprises an end of an optical fiber, whereby said optical fiber is capable of transmitting radiation of an appropriate exciting wavelength therethrough to said optical label and receiving therethrough a signal generated by said optical label.

10. A method according to claim 1 further comprising after step (e) of resynchronizing trailing oligo sequences by exposing said support-bound hybrid to a DNA polymerase in the presence of said nucleotide 5'-triphosphates wherein three of said nucleotides are blocked in the 3'-position and the fourth is unblocked in the 3'-position, said unblocked nucleotide corresponding to the nucleotide identified as having been added to said hybrid in the immediately preceding cycle.

* * * * *